United States Patent [19]

Mogi et al.

[11] Patent Number: 5,505,202
[45] Date of Patent: Apr. 9, 1996

[54] PORTABLE AND COLLAPSABLE ELECTROCARDIOGRAPH

[75] Inventors: Tomohiro Mogi, Tama; Kazutora Furukawa, Fussa; Hiroaki Suzuki, Hamura, all of Japan

[73] Assignee: Casio Computer Co., Ltd., Tokyo, Japan

[21] Appl. No.: 349,507

[22] Filed: Dec. 2, 1994

[30] Foreign Application Priority Data

Dec. 8, 1993 [JP] Japan .................................. 5-340611
Dec. 28, 1993 [JP] Japan .................................. 5-352026

[51] Int. Cl.$^6$ ............................... A61B 5/04; A61B 5/02
[52] U.S. Cl. ........................ 128/644; 128/640; 128/639
[58] Field of Search .................................. 128/639, 695, 128/696, 697, 700, 701, 709, 710, 711, 644, 642, 640, 731

[56] References Cited

U.S. PATENT DOCUMENTS

| | | | |
|---|---|---|---|
| 4,580,576 | 4/1986 | Blackwood | 128/696 X |
| 4,638,807 | 1/1987 | Ryder | 128/644 |
| 4,825,874 | 5/1989 | Uhlemann | 128/710 |
| 4,844,090 | 7/1989 | Sekine . | |
| 4,889,131 | 12/1989 | Salem et al. | 128/644 |
| 5,062,426 | 11/1991 | Ulbrich et al. | 128/640 |

FOREIGN PATENT DOCUMENTS 0265694 5/1988 European Pat. Off. .
2666977 3/1992 France .

*Primary Examiner*—Angela D. Sykes
*Assistant Examiner*—Stephen Huang
*Attorney, Agent, or Firm*—Frishauf, Holtz, Goodman, Langer & Chick

[57] ABSTRACT

In a portable electrocardiograph, a first measuring electrode that is to be held by a hand during measurement and comes into contact with the palm is provided on a body case. A second measuring electrode that to be pressed against the chest is provided on an arm member provided on the body case in foldable manner. The arm member is placed on the surface facing the body case when the arm member is folded onto the body case. Therefore, to measure electrocardiographic waves with this electrocardiograph, the user has only to slide the arm member into the opening between buttons on the front of his or her clothes or the opening in the shirt at the armpit, and then contacts the second measuring electrode with his chest for measurement. Therefore, it is not necessary to apply the apparatus perpendicularly to the chest. The user has only to place the apparatus almost in parallel to the chest and press the second measuring electrode against the left side of the heart in the chest. As a result, the user need not take off his or her clothes and can measure electrocardiographic waves easily and make quick measurement in case of heart attack. Furthermore, accurate measurement can also be effected.

12 Claims, 13 Drawing Sheets

PORTABLE AND COLLAPSABLE ELECTROCARDIOGRAPH

BACKGROUND OF THE INVENTION

1. Field of the Invention

This invention relates to an electrocardiograph, and more particularly to a portable electrocardiograph which enables a cardiopath to carry it with him or her and measure an electrocardiographic complex in case of unexpected heart attack.

2. Description of the Related Art

Since portable electrocardiographs are convenient for keeping track of the state of electrocardiographic waves in the cardiopath's everyday life, various types have been developed.

FIGS. 23 and 24 illustrate a conventional portable electrocardiographic-wave measuring apparatus. This electrocardiographic-wave measuring apparatus 100 has a case body 110 formed into the shape of a pencil. For portability, it can be put in and hung on a pocket with a clip 120 at one end of the case body 110. A first electrode 130 is provided on one end of the case body 110, and a second electrode 140 is provided on the surface of the middle portion of the case body 110. A press-button switch 150 is provided on the other end. Inside the case body 110, the electronic circuitry that measures electrocardiographic waves on the basis of the signals from the first and second electrodes 130 and 140 and a battery are housed.

FIG. 24 is an illustration to help explain how to use the electrocardiographic-wave measuring apparatus 100. Electrocardiographic waves are measured by pressing the first electrode 130 against the chest to the left side of the heart and pressing the switch 150, with the second electrode 140 on the surface of the body case 110 gripped with the right hand, for example. In this way, electrocardiographic waves can be measured whenever necessary.

However, the conventional electrocardiographic-wave measuring apparatus must have a relatively long body so that the user can hold it with his or her right hand and press the first electrode 130 against the chest. The conventional apparatus has another problem: depending on which part of the chest the first electrode 13 is pressed against and how the electrode is pressed against the chest, its contact resistance varies, and consequently the change in the contact resistance causes not only variations in the potential of the heart and noise, but also myoelectric noise attributable to muscular strain, preventing an accurate measurement of electrocardiographic waves. To solve this problem, as shown in FIG. 24, the electrocardiographic-wave measuring apparatus 100 must be pressed perpendicularly against the chest 170 to the left of the heart 170 at a suitable pressure. A shirt generally has buttons along its center line on the front, and therefore when something wrong has happened with his heart, the user must unbutton his shirt before pressing the electrocardiographic-wave measuring apparatus 100 against the chest 170 to the left side of his heart. In the case of clothes without buttons such as a pull-over sweater, the user has to take off the sweater, and therefore it takes him or her a lot of time to press the electrocardiographic-wave measuring apparatus 100 perpendicularly against the chest 170, preventing quick measurement. Especially for women, they may have to expose their chest in front of others for measurement and this will inflict mental pain on them.

SUMMARY OF THE INVENTION

Accordingly, the object of the present invention is to provide an electrocardiograph which has such a compact structure as enables the user to apply the apparatus to the chest without taking off his or her shirt and which therefore allows the user to measure the minute changes in each heartbeat easily and quickly.

The foregoing object is accomplished by providing an electrocardiograph comprising: a body section on which a first measuring electrode is provided; and an arm section provided on the body section in a foldable manner via a hinge section, with a second measuring electrode provided on the surface of the arm section facing the body section when the arm section is folded onto the body section.

With such a configuration, the present invention enables the user to measure electrocardiographic waves easily and quickly without taking off his or her clothes.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
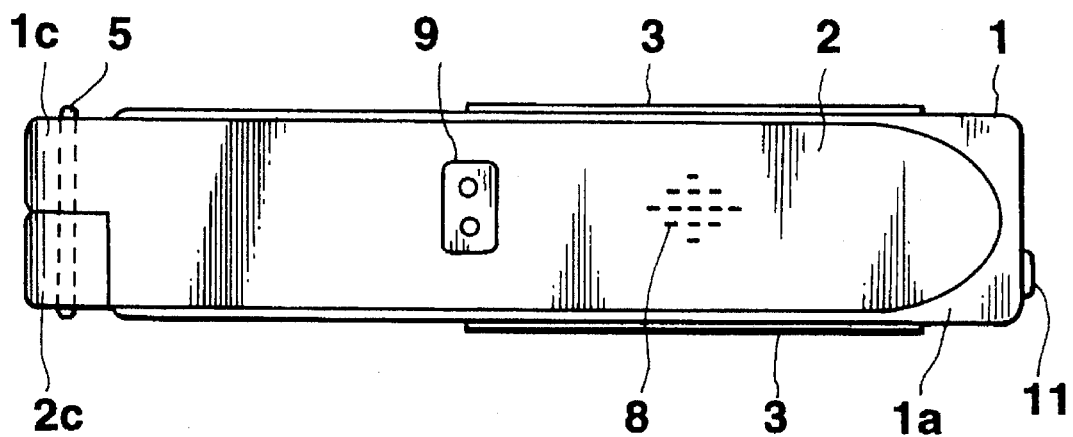
FIG. 1 is a plan view of an electrocardiograph in a folded state according a first embodiment of the present invention.
Figure 2:
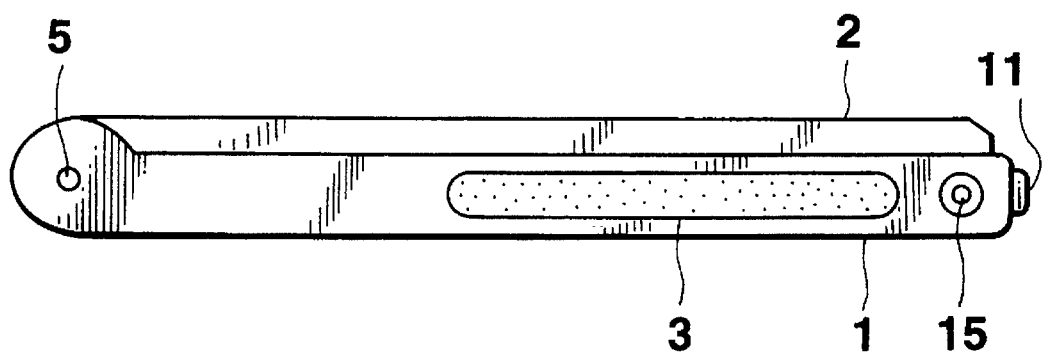
FIG. 2 is a side view of the electrocardiograph of FIG. 1.
Figure 3:
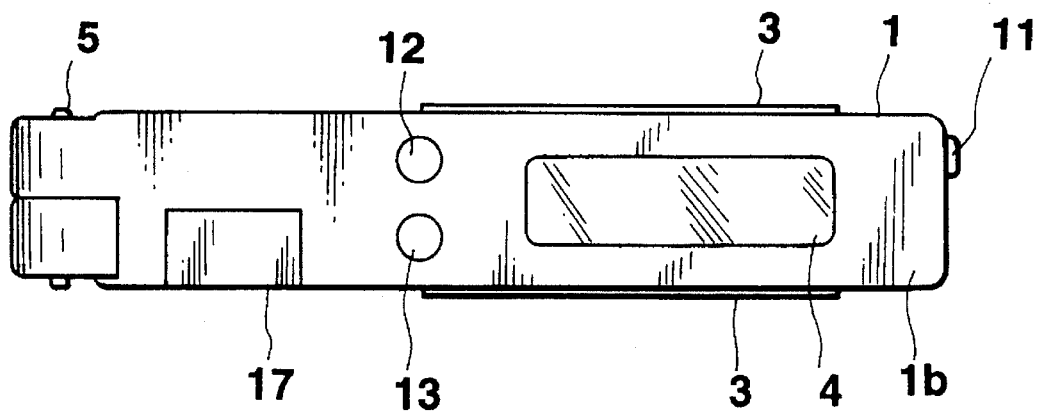
FIG. 3 is a bottom view of the electrocardiograph of FIG. 1.
Figure 4:
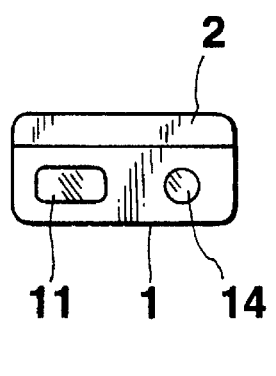
FIG. 4 is a right side view of the electrocardiograph of FIG. 1.
Figure 5:
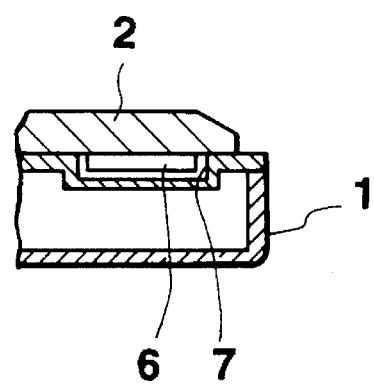
FIG. 5 is a partially sectional view of the electrocardiograph of FIG. 1 in a folded state.
Figure 6:
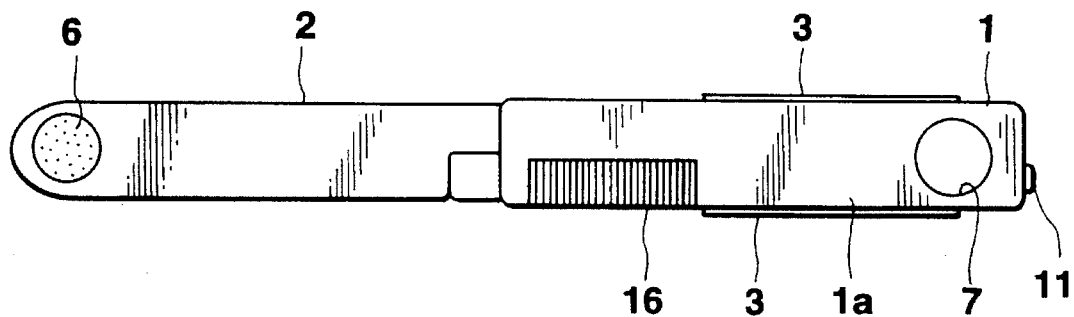
FIG. 6 is a plan view of the electrocardiograph in an expanded state.
Figure 7:
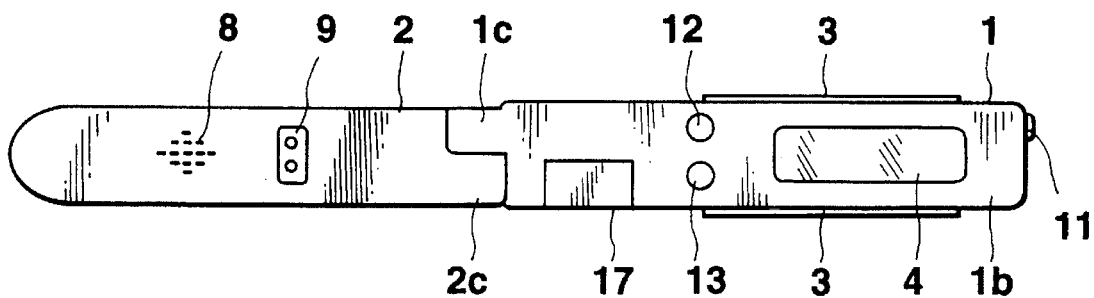
FIG. 7 is a bottom view of the electrocardiograph of FIG. 6.

FIGS. 1 to 10 show an embodiment of the present invention. An electrocardiographic-wave measuring apparatus 1 according to the embodiment has a folding structure. With this structure, the user carries the apparatus with him or her in a folded state as shown in FIGS. 1 and 2. When using it, he or she expands it as shown in FIGS. 6 and 7. A body case section 1A and an arm section 2 make up an outward form. The body case section 1A is shaped into a thin, flat rectangular parallelepiped. The arm section 2 is folded onto the top surface 1a of the body case section 1A with its one end (its left end) connected to the body case section 1A.

The body case section 1A has first measuring electrodes 3 provided on both sides of its longitudinal case. It also has a display member 4 on the bottom surface 1b opposite to the top surface 1a onto which the arm section 2 is folded. The display member 4 displays the stored data items including the electrocardiographic measurements, the time, and the telephone number. The arm section 2 is installed on the body case section 1A as follows: one end of the body case section 1A is cut away into half to form an ark-like hinge portion 1c, and similarly one end of the corresponding arm section 2 is cut away into half to form a hinge portion 2c; thereafter, these hinge portions 1c and 2c are placed side by side and pierced with a spring pin 5 for unity. This allows the arm section 2 to rotate around the spring pin 5, thereby changing the apparatus from the folded state to the expanded state. In the expanded state, electrocardiographic waves are measured.

To effect such measurement, a second measuring electrode 6 is provided on the arm section 2. The second measuring electrode 6 is placed at the tip portion of the arm section 2 as shown in FIG. 6. Measurement is made by pressing the electrode 6 against the chest. The second measuring electrode 6 is protruded to a specific height so as to enable contact with the chest, and is made of elastic conductive rubber, such as karaya gum, to ease a sense of contact with the skin. A recessed portion 7 is formed in the top surface 1a of the body case section 1A facing the second measuring electrode 6. When the arm section 2 is folded, the second measuring electrode 6 is housed in the recessed portion 7. This prevents the second measuring electrode 6 from being exposed to the outside and consequently dust from adhering to the electrode, thereby allowing accurate measurement. Furthermore, because there is no possibility that the electrode will interfere with another member, it will not be damaged. The first measuring electrode 3 may be made of the same material as that of the second measuring electrode 6 or another material such as metal.

As shown in FIGS. 6 and 7, the tip portion of the arm section 2 at which the second measuring electrode 6 is provided is shaped into an arc. This enables smooth insertion without getting caught in the clothes when the arm section 2 is inserted into the clothes for measurement. The display member 4 is located on the bottom surface 1b of the body case section 1A so as to be on the side opposite to the surface on which the second measuring electrode 6 is provided. This arrangement allows the user to look at the display member 4 during measurement, facilitating the visual checking of electrocardiographic data.

Figure 8:
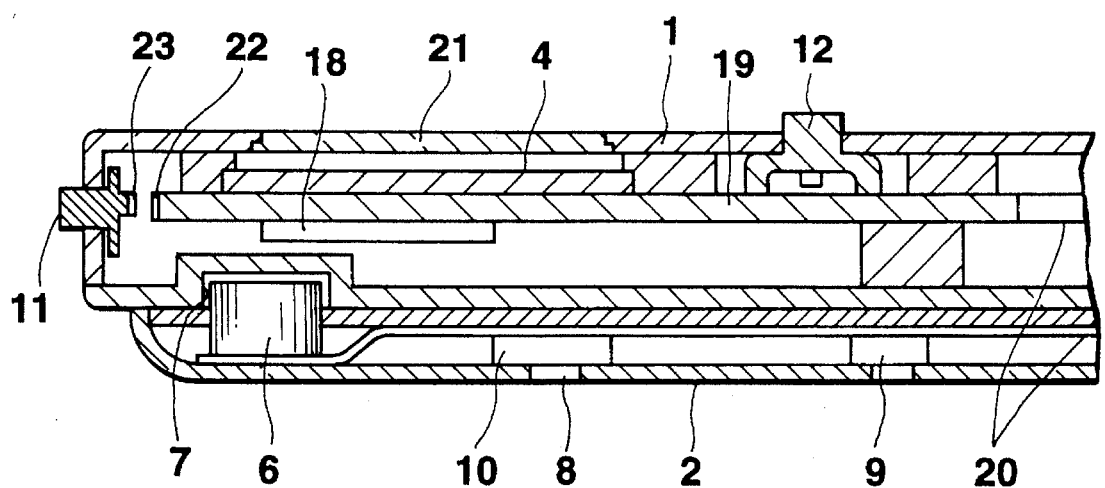
FIG. 8 is a sectional view of the internal configuration of the electrocardiograph of FIG. 1.

In FIGS. 1 and 7, numeral 8 indicates speaker perforations made in the opposite side of the arm section 2 to the second measuring electrode 6, and 9 indicates a communication member. As shown in FIG. 8, a speaker is placed inside the arm section 2 so as to correspond to the speaker perforations 8, which permits sound from the speaker to pass through during measurement or at the end of measurement. The communication member 9 is composed of, for example, a photocoupler provided with a phototransistor and a light-emitting diode. By mounting the electrocardiograph on the reading unit (not shown) of a medical instrument installed in a hospital, the electrocardiographic measurements are outputted to the unit. This enables the doctors in the hospital to grasp the electrocardiographic data on heartbeats during daily activities.

In FIGS. 1 to 4, numeral 11 indicates a first switch provided on the other end of the body case section 1A. The switch turns on and off the electrocardiographic measurement and also the communication by the communication member 9. Numerals 12 and 13 indicate second and third switches provided on the bottom surface of the body case section 1A, respectively. These switches 12 and 13 are used to correct the time, display the telephone numbers stored, or change to the communication mode. A light-emitting diode 14 for emitting light to indicate that measurement is now being made is placed adjacent to the first switch 11 (see FIG. 4). An electrode jack 15 to be connected to a commercial power supply for charging is provided on one longitudinal side of the body section 1 (see FIG. 2). On the top surface 1a of the body section 1, a battery cover 16 for replacing batteries (not shown) is provided (see FIG. 6). Furthermore, on the bottom surface of the body case section 1A, a switch cover 17 for protecting the internal switches (not shown) installed inside the body case section 1A is provided.

FIG. 8 illustrate an internal configuration of the present embodiment. Inside the body case section 1A, there is a circuit board 19 on which an LSI 18 for controlling the entire electrocardiograph is provided. The electrocardiographic measurements are supplied to the LSI 18 and the circuit board 19, which constitute an electric circuit member that outputs the electrocardiographic data to the display member 4 as a display signal. To achieve this, the circuit board 19 is connected to the second measuring electrode 6 via a flexible connecting board 20 extended from the body case section 1A to the inside of the arm section 2. The speaker 10 and the communication member 9 are mounted on the connecting board 20. The display member 4 is attached to the circuit board 19 and provides various indications as mentioned earlier. A film liquid-crystal member is used for the display member 4, which is therefore thin. Numeral 21 indicates a transparent plate made of glass or transparent plastic, provided on the body section 1 facing the display member 4. A fixed contact 22 is provided on one end of the circuit board 19. The fixed contact 22 is provided at a portion facing the first switch 11. When a movable contact 23 formed at the first switch 11 comes into contact with the fixed contact, this effects the aforementioned switching.

Figure 9:
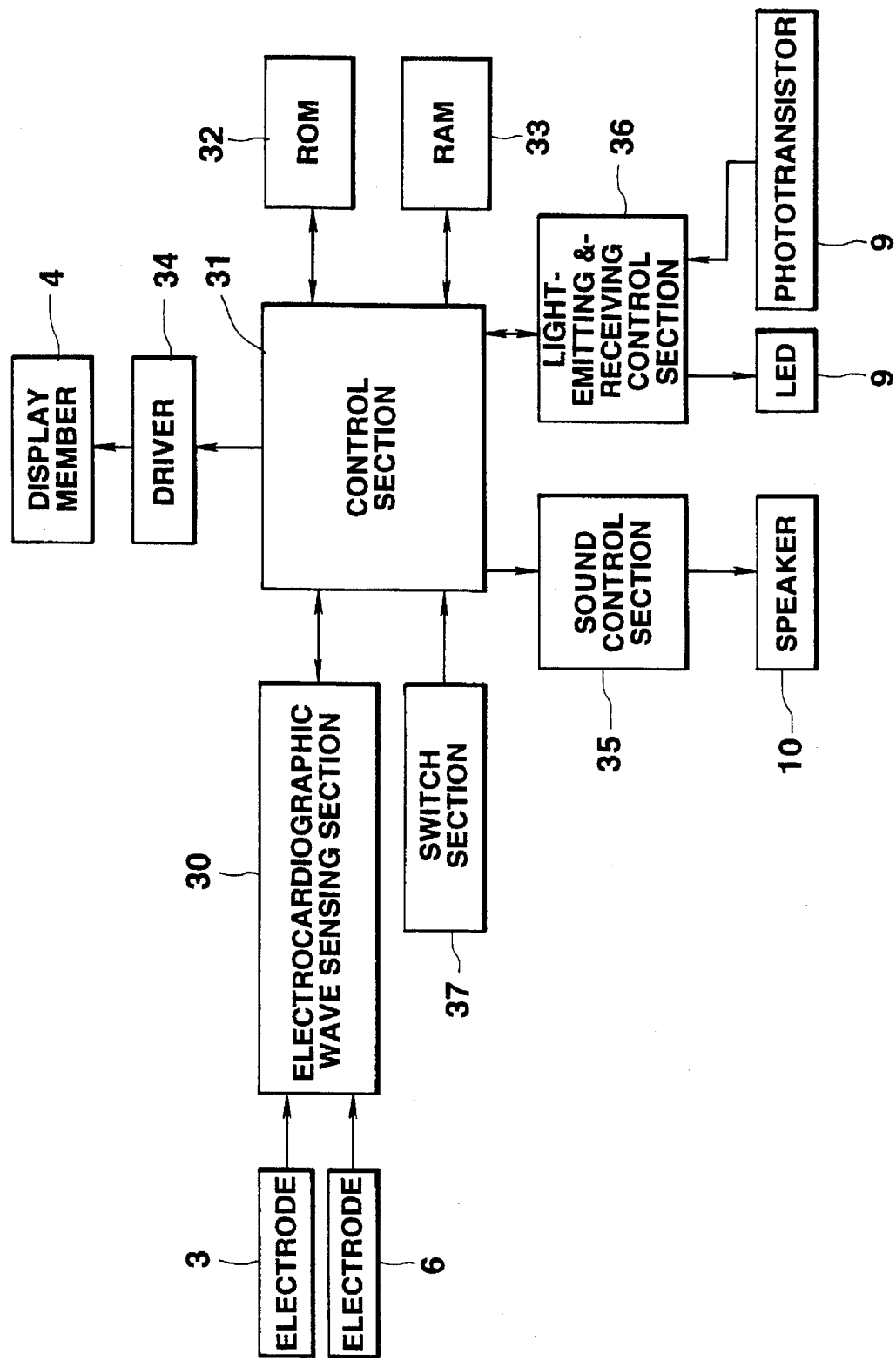
FIG. 9 is a block diagram of the electronic circuitry of the electrocardiograph in FIG. 1.

FIG. 9 is a block diagram of the internal electronic circuitry of the electrocardiograph according to the embodiment. The electronic circuitry comprises: a electrocardiographic-wave sensing section 30 to which the electrocardiographic waves measured by the first measuring electrode 3 and the second measuring electrode 6 are supplied; a control section 31 for controlling the operation of the electrocardiograph including each circuit; a ROM 32 in which microprograms are stored; a RAM 33 for storing a plurality of data; a driver 34 for controlling the indication on the display member 4; a sound control section 35 for driving the speaker 10, a light-emitting and -receiving control section 36 for controlling the communication member 39 including a photocoupler; and a switch section 37 for outputting the signals from the first to third switches 11, 12 and 13 to the control section 31.

The electrocardiographic-wave sensing section 30 senses and amplifies the electrocardiographic waves from the first and second measuring electrodes 3 and 6, filters the amplified electrocardiographic waves, analog-to-digital converts the filtered signals, and supplies the converted signals to the control section 31. Receiving the signals, the control section 31 controls the driver 34, which causes the display member 4 to provide an indication of plural electrocardiographic data. The control section 31 also stores the plural inputted electrocardiographic data in the RAM 33.

Figure 10:
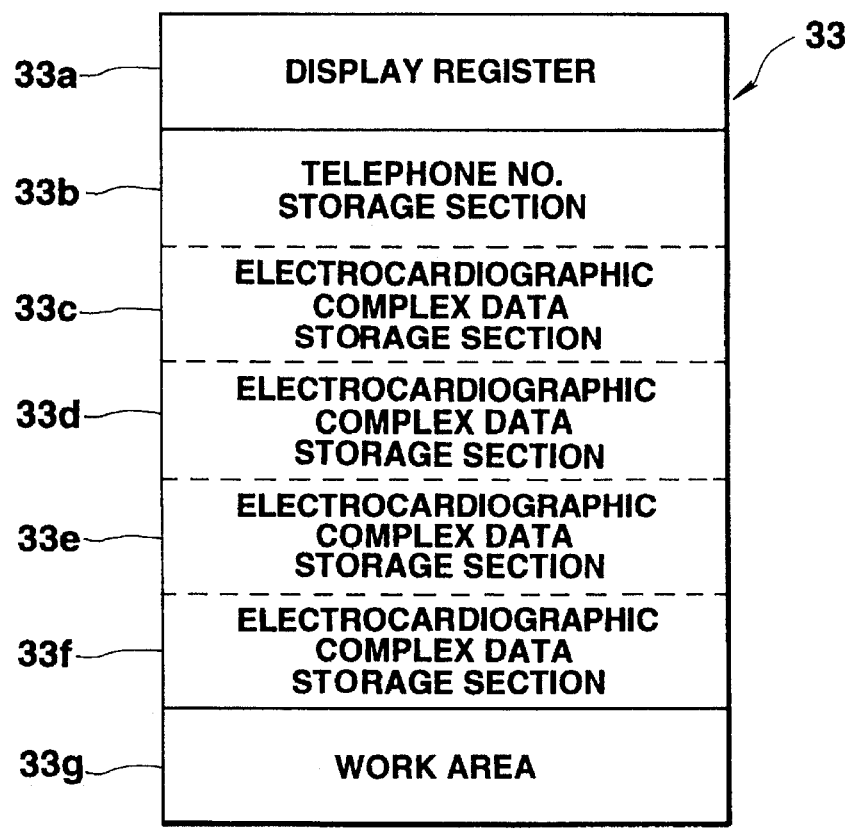
FIG. 10 shows the internal structure of the RAM in the electronic circuitry of FIG. 9.

FIG. 10 illustrates the internal structure of the RAM 33. The RAM 33 contains a display register 33a, a telephone number storage section 33b in which the telephone number of the owner of the electrocardiograph is stored, electrocardiographic complex data storage sections 33c, 33d, 33e and 33f in which the obtained electrocardiographic complex data is stored, and a work area 33g. In this embodiment, four areas are given to the electrocardiographic complex data storage sections 33c to 33f, which allow four measurements to be stored. The stored electrocardiographic data are read from the RAM 33 when necessary, and are displayed on the display member 4. They may be outputted from the communication member 9 to the outside.

With the embodiment, electrocardiographic waves are measured as follows: the user rotates the folded arm section 2 to expand it; he or she then, with the first measuring electrode 3 of the body case section 1 gripped by his or her right hand, slides the arm section 2 into the opening between buttons on the front of his or her clothes or the opening in the shirt at the armpit, or slides it inside from under the clothes; and thereafter, he or she contacts the second measuring electrode 6 with the chest for measurement. Therefore, it is not necessary to apply the apparatus perpendicularly to the chest. The user has only to place the apparatus almost in parallel to the chest and press the second measuring electrode 6 against the left side of the heart in the chest. As a result, the user need not take off his or her clothes and can measure electrocardiographic waves easily and make quick measurement in case of heart attack.

Figure 11:
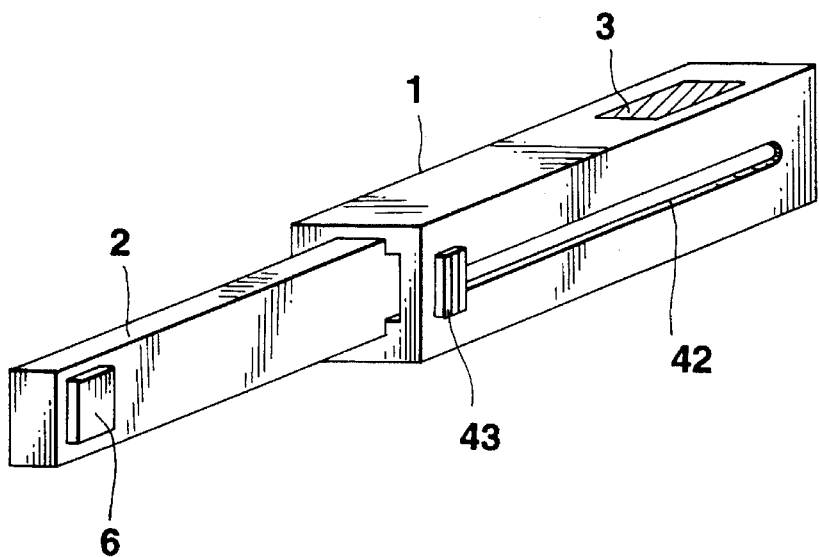
FIG. 11 is a perspective view of an electrocardiograph according to a second embodiment of the present invention.
Figure 12:
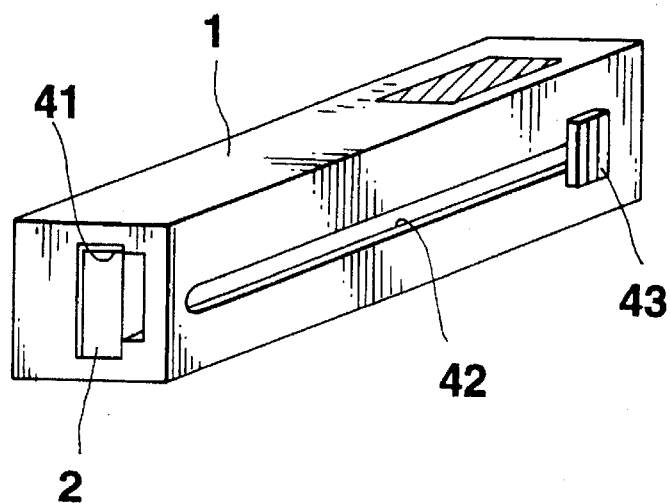
FIG. 12 is a perspective view of the electrocardiograph of FIG. 11 with the arm put back in place.
Figure 13:
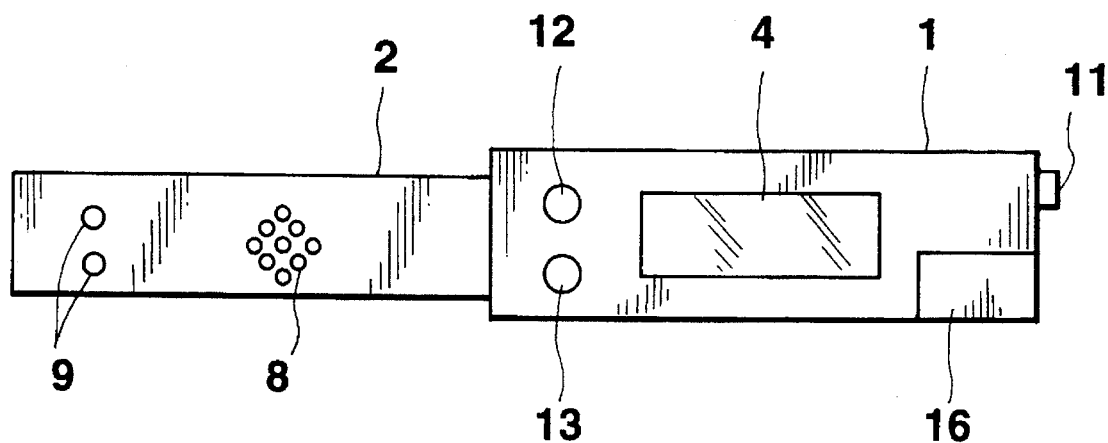
FIG. 13 is a plan view of the electrocardiograph of FIG. 11.
Figure 14:
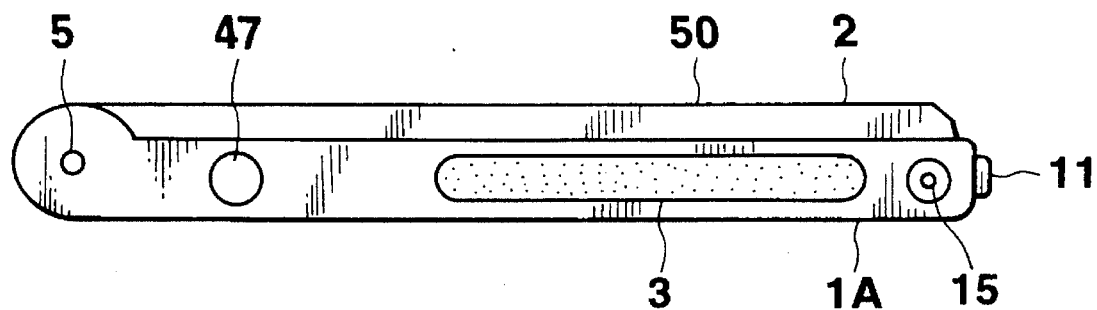
FIG. 14 is a side view of an electrocardiograph according to a third embodiment of the present invention.

FIGS. 11 to 13 show a second embodiment of the present invention. The same parts as those in the previous embodiment are indicated by the same reference symbols. In the second embodiment, the arm section 2 can be pulled out of or withdrawn into the body section 1 on which the first measuring electrode 3 is provided. To achieve this, an opening 41 through which the arm section 2 slides is made in one end of the body section 1. An oblong slit 42 is made in one longitudinal side of the body section 1. A slide switch 43 is provided in the slit 42. The slide switch 43 passes through the slit 42 and is connected to the arm section 2. Moving the slide switch 43 along the slit 42 withdraws the entire arm section 2 into the case body 1 for storage or pulls the arm section out of the case body 42 for expansion with the arm section expanded, electrocardiographic waves can be measured as in the previous embodiment.

Therefore, the second embodiment enables easy and quick measurement. Since the second measuring electrode 6 is housed in the case body 1, this prevents dust from adhering to the electrode.

The present invention is not limited to the above embodiments, but may be practiced or embodied in still other ways without departing from the spirit or essential character thereof. For instance, the display section 4 may be placed on the same side where the second measuring electrode 6 of the arm section 2 is. Furthermore, the communication member may be eliminated.

FIGS. 14 to 19 illustrate a third embodiment of the present invention. An electrocardiographic-wave measuring apparatus 50 according to the third embodiment has the same configuration as the electrocardiographic-wave measuring apparatus 1 shown in FIGS. 1 to 8, except that a connector terminal section 47 is provided on a side of the body case section 1A.

Figure 15:
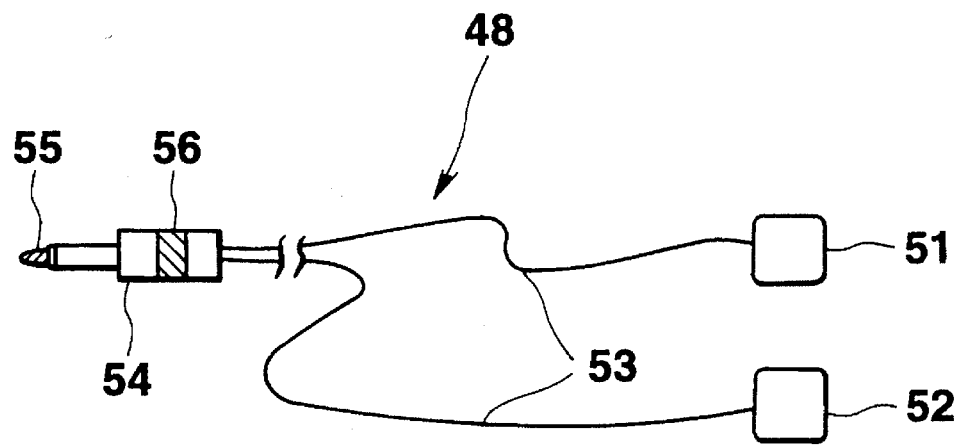
FIG. 15 is a plan view of an external connecting member to be connected to the electrocardiograph of FIG. 14.

To the connector terminal section 47, an external connecting member 48 shown in FIG. 15 is connected. The electrocardiographic-wave measuring apparatus 50 can measure electrocardiographic waves not only without connecting to any external circuit, but also in connection with the external connecting member 48.

FIG. 15 shows the external connecting member 48, which has first and second external electrodes 51 and 52 of conductive rubber or metal formed into a plate, and a pin jack 54 connected to connecting cords 53. The pin jack 54 is detachably inserted into the connector terminal 47 of the electrocardiographic-wave measuring apparatus 50. The insertion electrically connects the first and second external electrodes 51 and 52 to the electrocardiographic-wave measuring apparatus 50. To achieve such electrical connection, the pin jack 54 is provided with connecting electrodes 55 and 56 isolated from each other, which are connected to the external electrodes 51 and 52, respectively.

Figure 16:
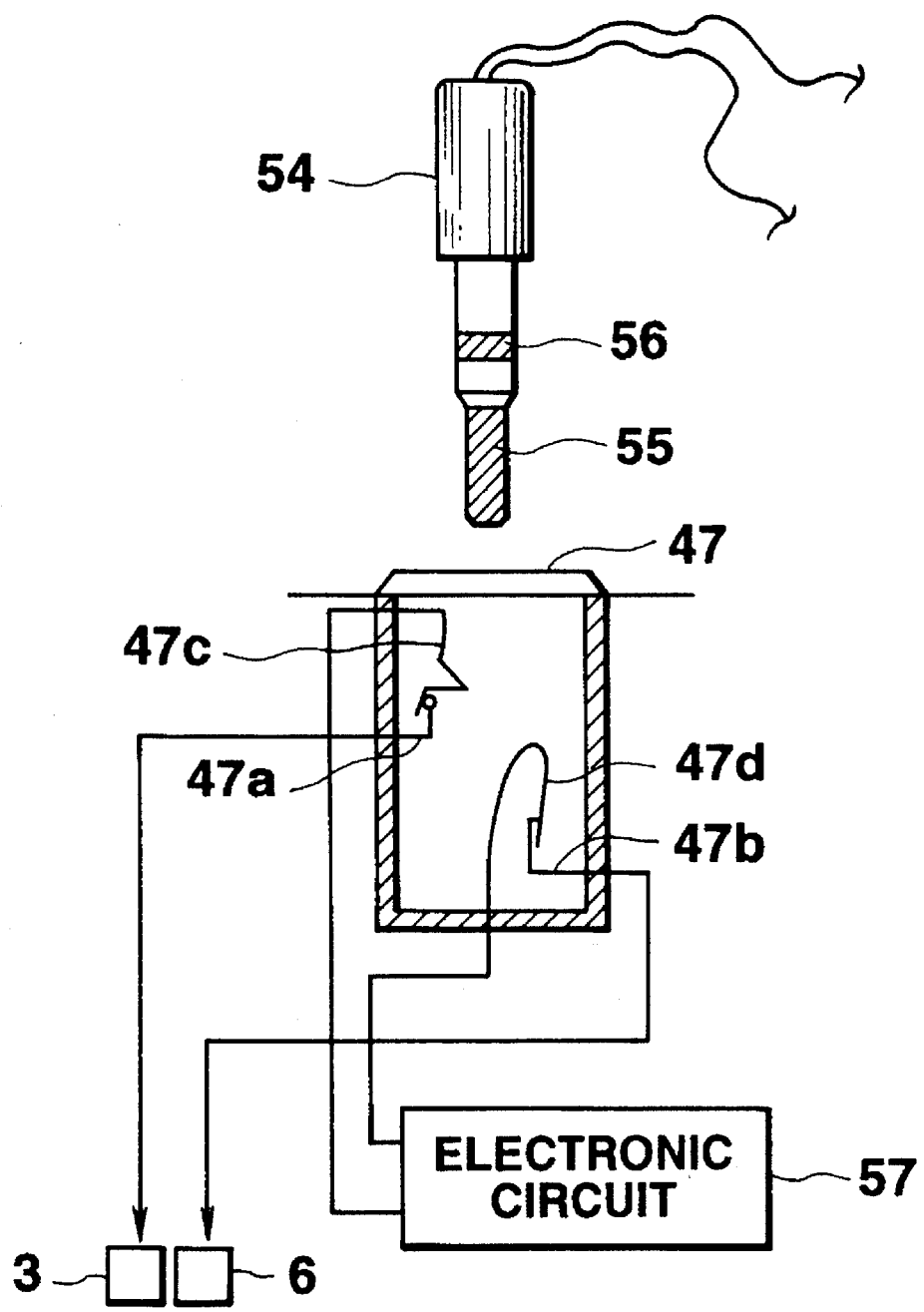
FIG. 16 illustrates the electrocardiograph before being connected to the external connecting member.
Figure 17:
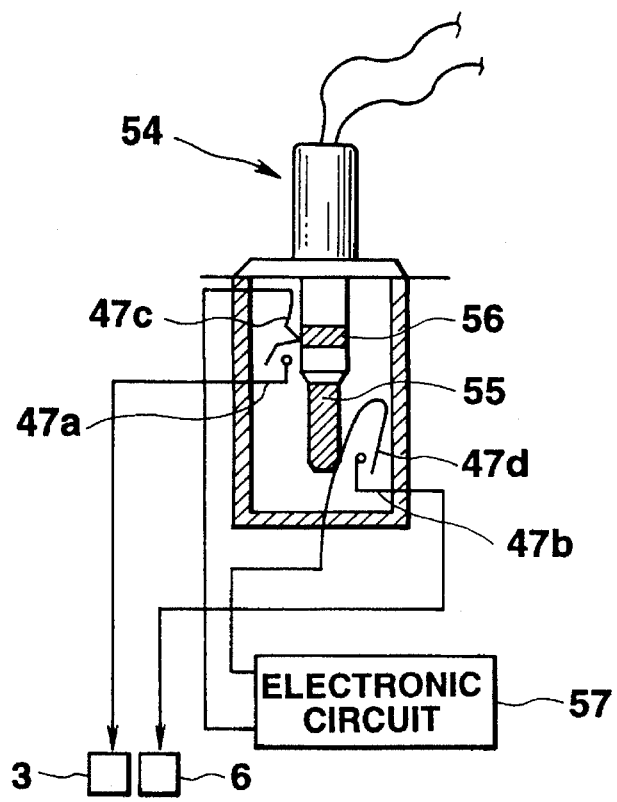
FIG. 17 illustrates the electrocardiograph after being connected to the external connecting member.

FIGS. 16 and 17 show the relationship between the connector terminal section 47 and the external connecting member 48. In the connector terminal section 47, there are provided terminal strips 47a and 47b electrically connected to the first and second measuring electrodes 3 and 6 respectively, and terminal strips 47c and 47d electrically connected to an electronic circuit 57 explained later. When the pin jack 54 is not inserted into the connector terminal section 47 as shown in FIG. 16, the terminal strips 47a and 47c and the terminal strips 47b and 47d are in contact with each other, thereby electrically connecting the first and second measuring electrodes 3 and 6 to the electronic circuit 57.

On the other hand, when the pin jack 54 is inserted into the connector terminal section 47 as shown in FIG. 17, the first connecting electrode 55 at the tip of the pin jack 54 comes into contact with the terminal strip 47d, while separating the terminal strip 47b from the terminal strip 47d. Additionally, the second connecting electrode 56 comes into contact with the terminal strip 47c, while separating the terminal strip 47a from the terminal strip 47c.

This connects the electronic circuit 57 to the external electrodes 51 and 52 of the external connecting member 48 via the first and second connecting electrodes 55 and 56. Therefore, with the pin jack 54 inserted in the connector terminal section 47, the electronic circuit 57 measures electrocardiographic waves on the basis of the signal transmitted from the external connecting section 48. In this case, the electronic circuit 57 measures electrocardiographic waves continuously as explained later.

Figure 18:
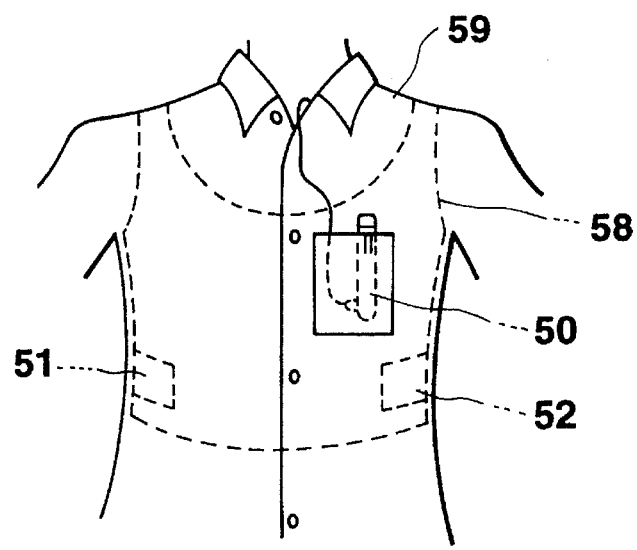
FIG. 18 is a front view of the user using the electrocardiograph.

FIG. 18 illustrates how the external connecting member 48 is used. The first and second external electrodes 51 and 52 of the external connecting member 48 are attached to the inside of the underclothes 58 that the user is going to wear so as to come in contact with the chest. After he or she has worn the underclothes 58, they are in contact with his or her body. In this state, with the pin jack 54 inserted into the connector terminal section 47 of the electrocardiographic-wave measuring apparatus 50 in the pocket of his or her jacket, signals are continuously transmitted from the first and second external electrodes 51 and 52 to the electrocardiographic-wave measuring apparatus 50. As a result, the electrocardiographic-wave measuring apparatus 50 can measure electrocardiographic waves continuously.

Figure 19:
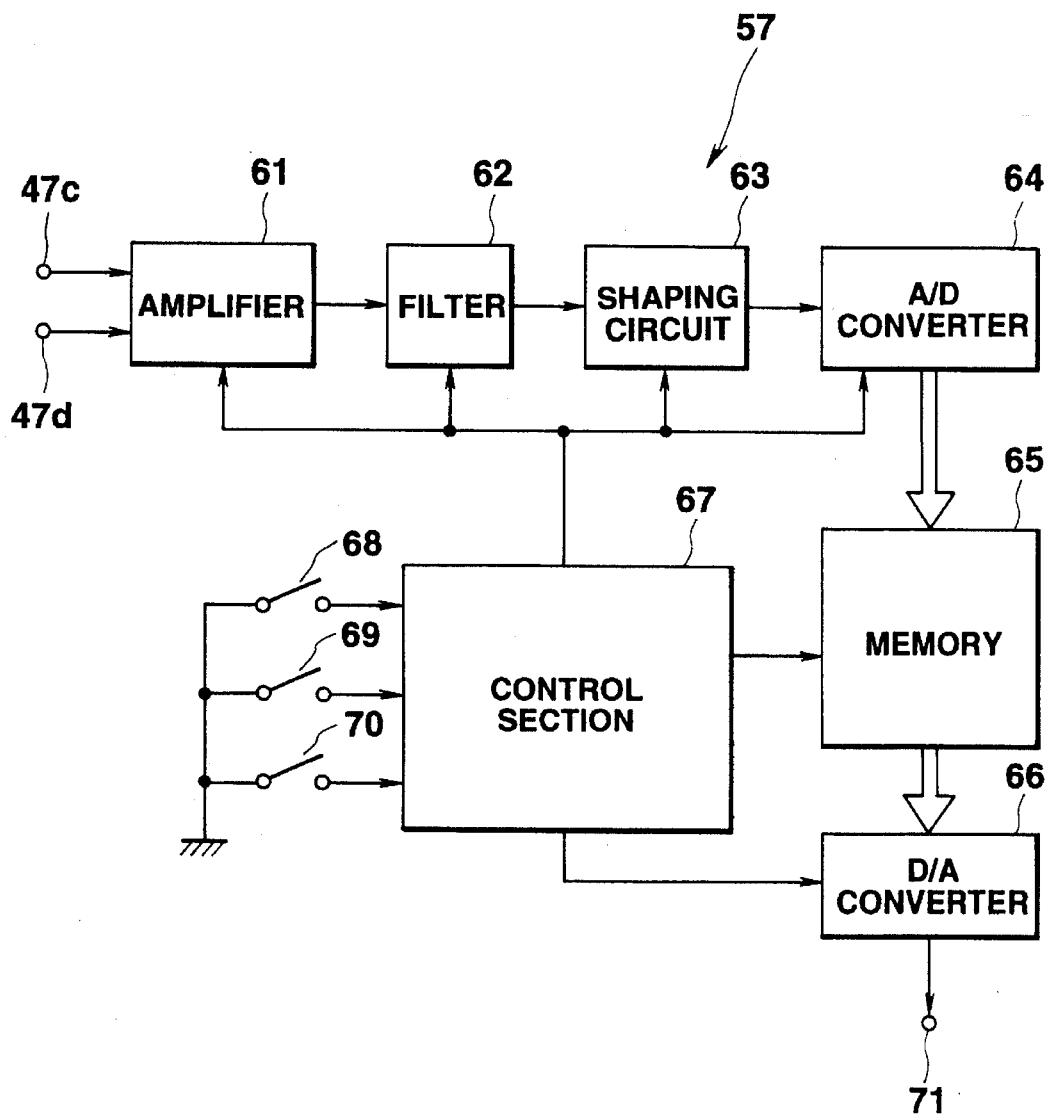
FIG. 19 is a block diagram of the electronic circuitry of the electrocardiograph.

FIG. 19 is a block diagram of the electronic circuit 57 that measures such electrocardiographic waves. In the figure, an amplifier circuit 61 amplifies electrocardiographic waves supplied from the terminal strips 47c and 47d. When the external connecting member 48 is connected to the connector terminal section 47, the amplifier circuit 61 receives electrocardiographic waves from the first and second external electrodes 51 and 52. When the external connecting member 48 is not connected to the connecting terminal section 47, the amplifier circuit 61 receives electrocardiographic waves from the measuring electrodes 3 and 6. A filter circuit 62 removes noise components from the amplified electrocardiographic waves at the amplifier circuit 61. A waveform-shaping circuit 63 shapes waveforms. After the shaped signal has been analog-to-digital converted at an A/D (analog/digital) converter circuit 64, the converted signal is stored in a memory 65.

A control section 67 controls each of the above circuits and is connected to a first, second, and third switches 68, 69, 70. When the first switch 68 is pressed, the control section 67 controls the memory 65 so that the memory may store the plural electrocardiographic complex data obtained in five measurements thereafter, and then stop the storing operation. When the second switch 69 is operated, with the external connecting member 48 connected to the connector terminal section 47, the control section 37 control the memory 65 so that the memory may store the electrocardiographic waves obtained in 200 measurements.

Furthermore, when the third switch 70 is operated, the control section 67 controls the memory 65 and a D/A converter circuit 66 to digital-to-analog convert the electrocardiographic waves stored in the memory 65, and supplies the converted signal at an output terminal 71 to the outside.

With the embodiment described above, the electrocardiographic-wave measuring apparatus 50 can not only measure electrocardiographic waves without connecting to any external circuit, but also measure electrocardiographic waves continuously in connection with the external connecting member 48. Since the external connecting member 48 measures electrocardiographic waves with the first and second external electrodes 51, 52 constantly in contact with the body, this provides better contact and therefore there is no variations in the potential of the heart. The user need not operate the electrocardiographic-wave measuring apparatus 50 each time he or she measures electrocardiographic waves, he or she does not experience muscular strain, and consequently myoelectric noise will not occur. As a result, accurate measurement can be effected. Since, with the apparatus connected to the external connecting member 48, electrocardiographic waves are measured continuously, this allows measurement of electrocardiographic waves in normal condition and also enables accurate diagnosis.

Figure 20:
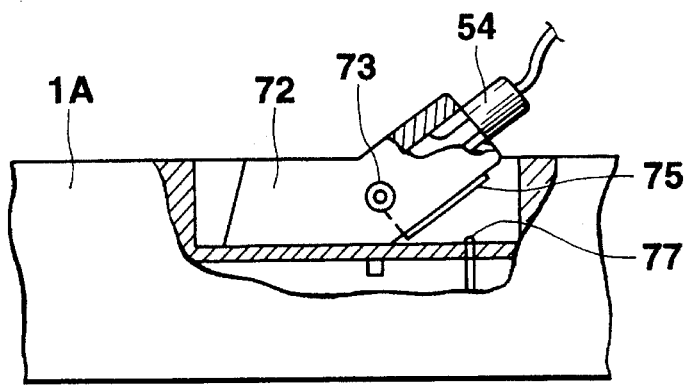
FIG. 20 illustrates the external connecting member connected to an electrocardiograph according to a fourth embodiment of the present invention.
Figure 21:
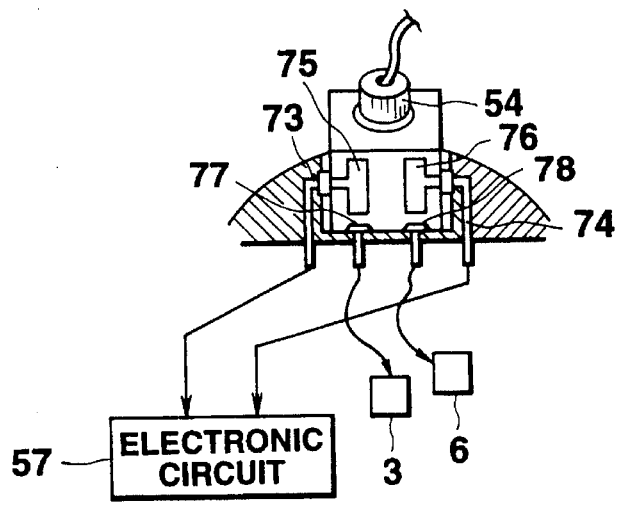
FIG. 21 is a sectional view of FIG. 20.
Figure 22:
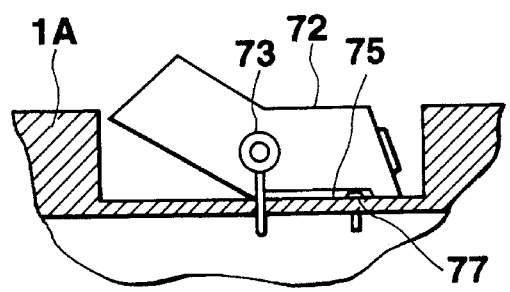
FIG. 22 is a side view of FIG. 20.
Figure 23:
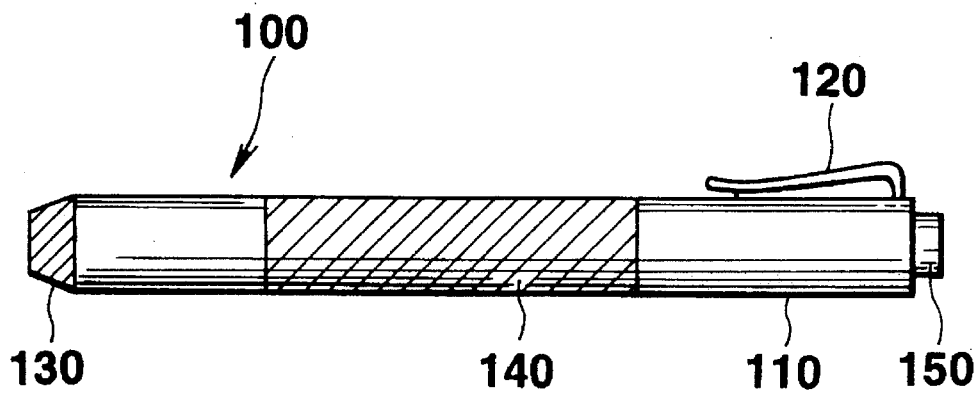
FIGS. 23 and 24 are diagrams to help explain the prior art.
Figure 24:
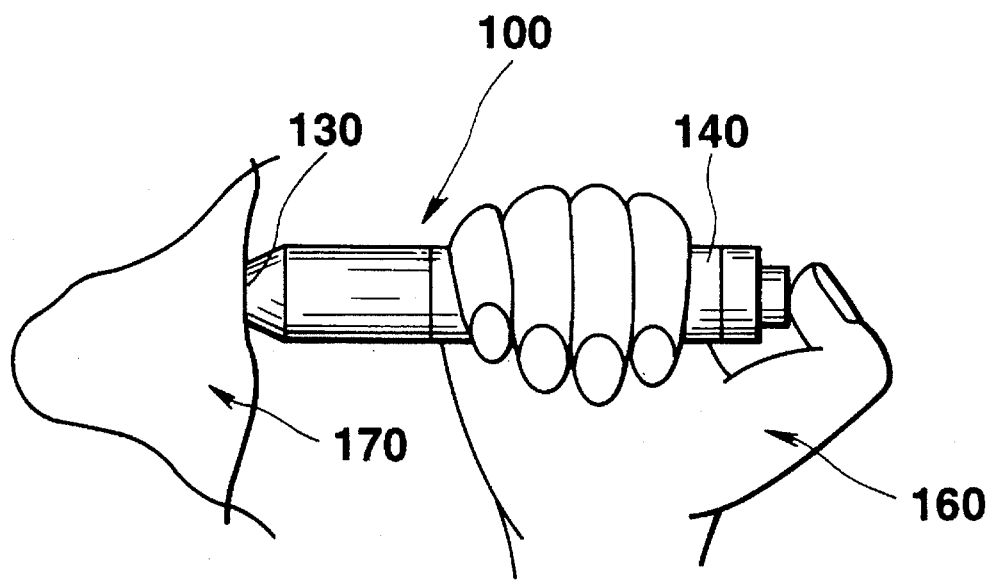

FIGS. 20 to 22 show a fourth embodiment of the present invention. This is another embodiment of the connector terminal section 47 in the third embodiment. In this embodiment, a connector terminal section 72 into which the pin jack 54 is inserted has its sides shaped into a dogleg and is designed to have a seesaw structure that can rotate with respect to the body case section 1A, with pins 73 and 74 supporting the terminal section. The pins 73 and 74 are connected to the electronic circuit 57 via leads as shown in FIG. 21. Terminal electrodes 75 and 76 are provided on the bottom surface of the connector section 72. Terminals 77 and 78 are provided on the body case section 1A so as to face the terminal electrodes 75 and 76, respectively. The terminals 77 and 78 are electrically connected to the measuring electrodes 3 and 6, respectively.

In this embodiment, with the pin jack 54 inserted into the connector terminal section-72 as shown in FIG. 20, the terminal electrodes 75. 76 are separated from the terminals 77, 78, which connects the external connecting member 48 to the electronic circuit 57. Then, the electronic circuit 57 measures electrocardiographic waves continuously. In contrast, when the pin jack 54 is not inserted, the connector terminal section 72 can be rotated. This allows the terminal electrodes 75 and 76 to come into contact with the terminals 77 and 78 as shown in FIG. 22. Therefore, in the state of FIG. 22, electrocardiographic waves are measured from the signals from the measuring electrodes 3 and 6.

As described above, with the present embodiment, by connecting the external connecting member, electrocardiographic waves can be measured accurately and continuously, and furthermore accurate diagnosis can be performed.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A portable electrocardiograph comprising:

a longitudinal body section provided with a first measuring electrode, said body section having two ends;

a hinge section provided at one end of said body section;

a longitudinal arm section having:
one end portion coupled with said body section via said hinge section such that said arm section is movable between two positions corresponding respectively to a folded state and an unfolded state in relation to said body section, said arm section extending from said body section when said arm section is in said unfolded state; and
another end portion; and a second measuring electrode provided on said another end portion of said arm section and on a surface of said arm section facing said body section when said arm section is in said folded state wherein said arm section is folded onto said body section, and wherein when said arm section is in the unfolded state with respect to said body section a portion of said body section on which the first measuring electrode is provided is held by a hand of a user such that the hand of the user contacts the first measuring electrode, and said second measuring electrode is in contact with a chest of the user, when cardiographic waves are measured.

2. A portable electrocardiograph according to claim 1, wherein said body section has a recessed portion that houses said second measuring electrode of said arm section when said arm section is in said folded state.

3. A portable electrocardiograph according to claim 1, wherein:
said first and second measuring electrodes are electrodes for measuring electrocardiographic-wave data; and
said body section comprises display means for displaying electrocardiographic-wave data measured by said first and second measuring electrodes.

4. A portable electrocardiograph according to claim 3, wherein said display means comprises a liquid crystal display.

5. A portable electrocardiograph according to claim 1, wherein:
said first and second measuring electrodes are electrodes for measuring electrocardiographic-wave data; and
said body section comprises storage means for storing electrocardiographic-wave data measured by said first and second measuring electrodes.

6. A portable electrocardiograph according to claim 5, further comprising output means for optically outputting electrocardiographic-wave data stored in said storage means.

7. A portable electrocardiograph comprising:
a body section provided with a first measuring electrode and a display member for displaying electrocardiographic-wave data;
an arm section provided in said body section such that the arm section can be withdrawn into and pulled out of said body section, said arm section having a second measuring electrode;
said first and second measuring electrodes being arranged to measure electrocardiographic-wave data; and
an electronic circuit member which receives electrocardiographic-wave data measured by said first and second measuring electrodes and supplies a display signal to said display member.

8. A portable electrocardiograph according to claim 7, wherein:
said second measuring electrode is provided on a surface of said arm section; and
said display member is provided on a surface of said body section opposite to the surface of said arm section on which said second measuring electrode is provided.

9. A portable electrocardiograph according to claim 7, further comprising a communication member for outputting the electrocardiographic-wave data inputted to said electronic circuit member to an external unit.

10. A portable electrocardiograph comprising:
a longitudinal case body on which a first measuring electrode and a connector terminal are provided, said case body having two end portions;
a hinge section provided on one end portion of said case body;
a longitudinal arm section having:
one end portion coupled with said case body via said hinge section such that said arm section is movable between two positions corresponding respectively to a folded state and an unfolded state in relation to said case body, said arm section extending from said case body when said arm section is in said unfolded state; and
another end portion;
a second measuring electrode provided on said another end portion of said arm section and on a surface of said arm section facing said case body when said arm section is in said folded state wherein said arm section is folded onto said case body;
an external connecting member arranged to be connected to said connector terminal; and
an electrocardiographic-wave measuring circuit for measuring, when said arm section is in said unfolded state at a position extended from said case body the electrocardiographic-waves in a state where a portion of said case body on which said first measuring electrode is provided is held by a hand of a user and said second measuring electrode is in contact with a chest of the user, and for measuring, when said arm section is in said folded state wherein it is folded onto said case body, the electrocardiographic-waves in accordance with a signal transferred to the electrocardiographic-wave measuring circuit via said external connecting member when said external connecting member is connected to said connector terminal.

11. A portable electrocardiograph according to claim 10, wherein said electrocardiographic-wave measuring circuit measures electrocardiographic-waves continuously when said external connecting member is connected to said connector terminal, based on signals received from said external connecting member.

12. A portable electrocardiograph according to claim 10, wherein:
said connector terminal comprises a pin jack; and
said external connecting member comprises:
a sensor which is applied to a body portion of the user and which senses electrocardiographic-waves; and
means for connecting said sensor to said pin jack.

* * * * *